US012773315B2

(12) United States Patent
Montgomery et al.

(10) Patent No.: US 12,773,315 B2
(45) **Date of Patent: *Oct. 27, 2026**

(54) VALVE DELIVERY SYSTEM INCLUDING FORESHORTENING COMPENSATOR FOR IMPROVED POSITIONING ACCURACY

(71) Applicant: Medtronic CV Luxembourg S.a.r.l., Luxembourg (LU)

(72) Inventors: Stephen Montgomery, Galway (IE); Maro Sciacchitano, Galway (IE)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 45 days.

This patent is subject to a terminal disclaimer.

(21) Appl. No.: 18/953,733

(22) Filed: Nov. 20, 2024

(65) Prior Publication Data

US 2025/0082471 A1 Mar. 13, 2025

Related U.S. Application Data

(60) Continuation of application No. 18/181,941, filed on Mar. 10, 2023, now Pat. No. 12,178,701, which is a (Continued)

(51) Int. Cl.

| | |
|---|---|
| ***A61F 2/24*** | (2006.01) |
| *A61B 17/00* | (2006.01) |
| *A61M 25/01* | (2006.01) |

(52) U.S. Cl.

CPC .......... *A61F 2/2436* (2013.01); *A61F 2/2418* (2013.01); *A61B 2017/00318* (2013.01); *A61F 2210/0014* (2013.01); *A61M 25/0136* (2013.01)

(58) Field of Classification Search

CPC .. A61F 2/2427; A61F 2/2436; A61M 25/0136

See application file for complete search history.

(56) References Cited

U.S. PATENT DOCUMENTS

| | | | |
|---|---|---|---|
| 7,935,141 | B2 | 5/2011 | Randall et al. |
| 8,523,064 | B1 | 9/2013 | Bucheit et al. |

(Continued)

FOREIGN PATENT DOCUMENTS

| | | | |
|---|---|---|---|
| WO | 2015/038875 | A1 | 3/2015 |
| WO | 2019/199533 | A1 | 10/2019 |

OTHER PUBLICATIONS

International Search Report and Written Opinion mailed Jan. 20, 2021, Intl. Appl. No. PCT/EP2020/078236.

*Primary Examiner* — Todd J Scherbel

(74) *Attorney, Agent, or Firm* — MEDLER FERRO WOODHOUSE & MILLS PLLC

(57) ABSTRACT

A system including a self-expanding prosthesis configured to foreshorten during deployment thereof and a delivery device configured to percutaneously deliver the self-expanding prosthesis. The delivery device includes a handle having an actuator thereon, an outer sheath including a proximal end coupled to the handle and a pusher shaft slidingly disposed within the outer sheath. The pusher shaft has a proximal end coupled to the handle and a distal end configured to releasably couple to the self-expanding prosthesis such that the self-expanding prosthesis axially moves therewith. The inner shaft has a distal portion of the inner shaft that is configured to receive a self-expanding prosthesis thereon. The outer sheath and the pusher shaft are configured to simultaneously move in opposing axial directions via actuation of the actuator on the handle to compensate for the foreshortening of the self-expanding prosthesis during deployment.

19 Claims, 9 Drawing Sheets

Related U.S. Application Data division of application No. 16/596,937, filed on Oct. 9, 2019, now Pat. No. 11,622,858.

(56) References Cited

U.S. PATENT DOCUMENTS

| | | | | |
|---|---|---|---|---|
| 8,585,750 | B2 | 11/2013 | Argentine | |
| 8,747,448 | B2 | 6/2014 | Argentine | |
| 9,445,928 | B2 | 9/2016 | Argentine | |
| 9,486,350 | B2 | 11/2016 | Argentine | |
| 10,406,012 | B2 | 9/2019 | Argentine | |
| 10,433,995 | B2 | 10/2019 | Argentine | |
| 11,622,858 | B2 * | 4/2023 | Montgomery .......... | A61F 2/966<br>623/2.11 |
| 12,178,701 | B2 * | 12/2024 | Montgomery .......... | A61F 2/966 |
| 2002/0111666 | A1 | 8/2002 | Hart et al. | |
| 2003/0191516 | A1 | 10/2003 | Weldon et al. | |
| 2004/0127912 | A1 | 7/2004 | Rabkin et al. | |
| 2009/0018553 | A1 | 1/2009 | Mclean et al. | |
| 2009/0099638 | A1 | 4/2009 | Grewe | |
| 2010/0036472 | A1 | 2/2010 | Papp | |
| 2010/0168756 | A1 | 7/2010 | Dorn et al. | |
| 2010/0174290 | A1 | 7/2010 | Wuebbeling et al. | |
| 2011/0172765 | A1 | 7/2011 | Nguyen et al. | |
| 2011/0251681 | A1 | 10/2011 | Shipley et al. | |
| 2011/0282425 | A1 | 11/2011 | Dwork | |
| 2012/0035722 | A1 | 2/2012 | Tuval | |
| 2012/0053574 | A1 | 3/2012 | Murray, III et al. | |
| 2012/0101572 | A1 | 4/2012 | Kovalsky et al. | |
| 2013/0331925 | A1 | 12/2013 | Roeder et al. | |
| 2014/0046429 | A1 | 2/2014 | Cragg et al. | |
| 2015/0265445 | A1 | 9/2015 | Weber et al. | |
| 2015/0305902 | A1 | 10/2015 | Argentine | |
| 2016/0120677 | A1 | 5/2016 | Heanue et al. | |
| 2019/0298557 | A1 | 10/2019 | Murray, III | |
| 2019/0314178 | A1 | 10/2019 | Sethna et al. | |

* cited by examiner

VALVE DELIVERY SYSTEM INCLUDING FORESHORTENING COMPENSATOR FOR IMPROVED POSITIONING ACCURACY

CROSS-REFERENCE TO RELATED APPLICATIONS

This application is a continuation of U.S. patent application Ser. No. 18/181,941, filed Mar. 10, 2023, now allowed, which is a divisional of U.S. patent application Ser. No. 16/596,937, filed Oct. 9, 2019, now U.S. Pat. No. 11,622,858, which is hereby incorporated by reference in its entirety for all purposes.

FIELD OF THE INVENTION

The present invention is related to delivery systems and methods of delivering a self-expanding prostheses.

BACKGROUND

Prostheses for implantation in blood vessels or other similar organs of the living body are, in general, well known in the medical art. For example, prosthetic vascular stent-grafts constructed of biocompatible materials have been employed to replace or bypass damaged or occluded natural blood vessels. In general, prosthetic vascular stent-grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, prosthetic vascular stent-grafts are typically held in place by mechanical engagement and friction due to the opposition forces provided by the radially expandable stents. In another example, expandable stents may be deployed without the addition of a covering graft component. Further, prosthetic valves supported by stent structures have also been developed for heart and venous valve replacement.

In general, rather than performing an open surgical procedure that may be traumatic and invasive, prostheses are preferably deployed through a less invasive intraluminal delivery procedure. More particularly, a lumen or vasculature is accessed percutaneously at a convenient and less traumatic entry point, and the prosthesis is routed through the vasculature to the site where the prosthesis is to be deployed. Intraluminal deployment is typically affected using a delivery catheter with coaxial inner and outer tubes arranged for relative axial movement. For example, a self-expanding prosthesis may be compressed and disposed within the distal end of an outer catheter tube. The catheter is then maneuvered, typically routed through a body lumen until the end of the catheter and the prosthesis are positioned at the intended treatment site. The inner member is then held stationary while the outer tube of the delivery catheter is withdrawn. A stop may be utilized to prevent the prosthesis from being withdrawn with the sheath. As the sheath is withdrawn, the prosthesis is released from the confines of the sheath and radially self-expands so that at least a portion of the prosthesis contacts and substantially conforms to a portion of the surrounding interior of the lumen, e.g., the blood vessel wall or anatomical conduit.

Self-expanding prostheses often foreshorten or longitudinally contract during deployment, and such foreshortening may result in difficulty in accurately positioning the self-expanding prosthesis. Embodiments hereof relate to a delivery system that is configured to compensate for the foreshortening of the self-expanding prosthesis during deployment to ensure accurate positioning thereof.

SUMMARY

Embodiments of the present invention relate generally to delivery systems, and, more specifically to a delivery device for percutaneously delivering a self-expanding prosthesis. The delivery device includes a handle having an actuator thereon, an outer sheath including a proximal end operatively coupled to the handle, a pusher shaft slidingly disposed within the outer sheath, and an inner shaft disposed within the pusher shaft. The pusher shaft has a proximal end operatively coupled to the handle. The inner shaft has a distal portion of the inner shaft that is configured to receive a self-expanding prosthesis thereon. The outer sheath and the pusher shaft are configured to simultaneously move in opposing axial directions via actuation of the actuator on the handle.

Embodiments hereof also relate to a system that includes a self-expanding prosthesis configured to foreshorten during deployment thereof and a delivery device configured to percutaneously deliver the self-expanding prosthesis. The delivery device includes a handle having an actuator thereon, an outer sheath including a proximal end coupled to the handle, a pusher shaft slidingly disposed within the outer sheath, and an inner shaft disposed within the pusher shaft. The pusher shaft has a proximal end coupled to the handle and a distal end configured to releasably couple to the self-expanding prosthesis such that the self-expanding prosthesis axially moves therewith. The inner shaft has a distal portion of the inner shaft that is configured to receive a self-expanding prosthesis thereon. The outer sheath and the pusher shaft are configured to simultaneously move in opposing axial directions via actuation of the actuator on the handle to compensate for the foreshortening of the self-expanding prosthesis during deployment.

Embodiments hereof also relate to a method of delivering a self-expanding heart valve prosthesis to a treatment site within the vasculature of a patient using a delivery device comprising an outer sheath, a pusher shaft, and an inner shaft. The delivery device is delivered to the treatment site such that a proximal end of the self-expanding heart valve prosthesis is positioned at an annulus of a native heart valve. The self-expanding heart valve prosthesis is deployed at the annulus of a native heart valve. The self-expanding heart valve prosthesis foreshortens during deployment. The outer sheath is proximally retracted and the pusher shaft is simultaneously distally advanced as the self-expanding heart valve prosthesis is deployed in order to compensate for the foreshortening of the self-expanding heart valve prosthesis.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant art(s) to make, use, and implant the prosthesis described herein. In the drawings, like reference numbers indicate identical or functionally similar elements.

DETAILED DESCRIPTION OF THE INVENTION

Figure 1:
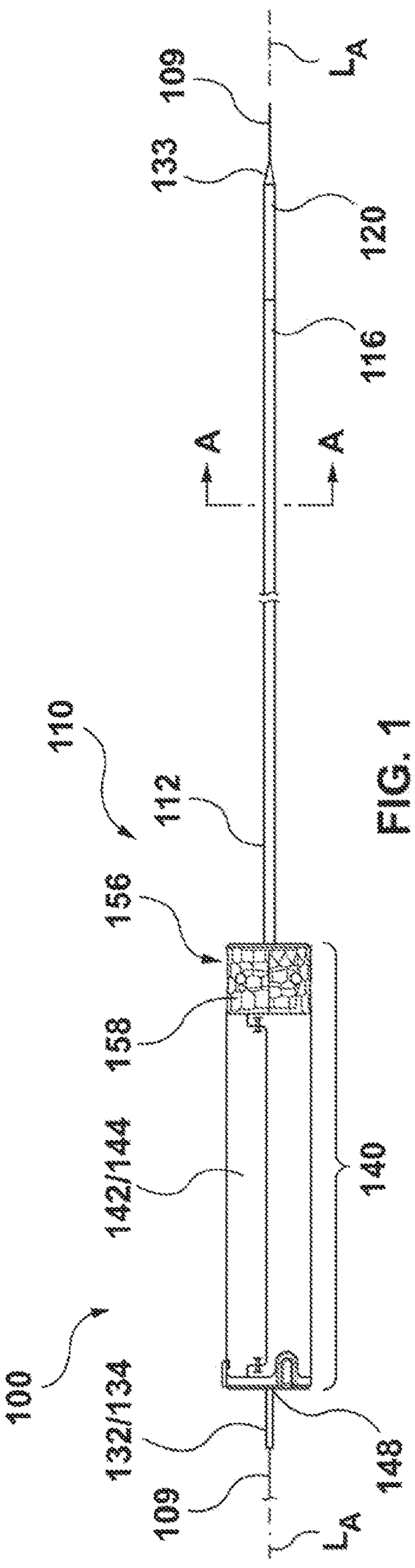
FIG. 1 is a side view of a delivery system according to an embodiment hereof, wherein the delivery system is in a delivery configuration.

Specific embodiments of the present invention are now described with reference to the figures, wherein like reference numbers indicate identical or functionally similar elements. Unless otherwise indicated, for the delivery system the terms “distal” and “proximal” are used in the following description with respect to a position or direction relative to the treating clinician. “Distal” and “distally” are positions distant from or in a direction away from the clinician, and “proximal” and “proximally” are positions near or in a direction toward the clinician. For the prosthesis “proximal” is the portion nearer the heart by way of blood flow path while “distal” is the portion of the prosthesis further from the heart by way of blood flow path. In addition, the term “self-expanding” is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely illustrative in nature and is not intended to limit the invention or the application and uses of the invention. Although the description of the invention is primarily in the context of treatment of a heart valve, the invention may also be used in any body passageway where it is deemed useful. For example, the invention may be used with any self-expanding prosthesis that is configured to foreshorten during deployment and may be used in any body passageway where such self-expanding prosthesis is deemed useful. As used herein, “prosthesis” or “prostheses” may include any prosthesis including one or more self-expanding structures, including but not limited to heart valve prostheses, stents, stent-graft prostheses, uncovered stents, bare metal stents, drug eluting stents, and any self-expanding structure that is configured to foreshorten during deployment.

Embodiments hereof relate to a delivery device with improved positioning accuracy for percutaneously delivering a self-expanding prosthesis. Self-expanding prostheses often foreshorten during deployment. Stated another way, a length of a self-expanding prosthesis in a delivery or compressed configuration is often longer than a length of the self-expanding prosthesis in a deployed or expanded configuration. Such foreshortening may result in difficulty in accurately positioning the self-expanding prosthesis due to the fact that after being positioned at a target location by a clinician, the self-expanding prosthesis may move away from the target location in situ during deployment thereof. Embodiments hereof relate to a delivery system that is configured to compensate for the foreshortening of the self-expanding prosthesis during deployment to ensure accurate positioning thereof. The clinician is not required to adjust the position of the self-expanding prosthesis during deployment, and thus the delivery system reduces reliance on clinician experience and performance. In addition, embodiments of the delivery system described herein reduces the force exerted on the interface between the delivery device and the self-expanding prosthesis since the self-expanding prosthesis is not held stationary at such interface. More particularly, when the self-expanding prosthesis is configured to foreshorten during deployment, a force up to 9 N may be exerted on the interface between the delivery device and the self-expanding prosthesis when the self-expanding prosthesis is forced to remain stationary during deployment. However, in embodiments hereof, the self-expanding prosthesis is distally advanced during deployment to compensate for the foreshortening thereof and forces at the interface between the delivery device and the self-expanding prosthesis are reduced or minimized.

Figure 1A:
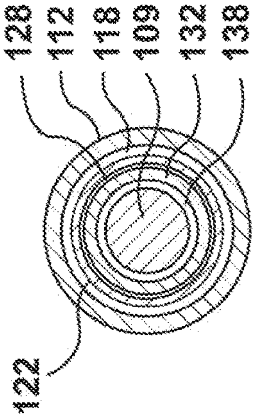
FIG. 1A is a cross-sectional view of the delivery system of FIG. 1 taken along line A-A of FIG. 1.
Figure 2:
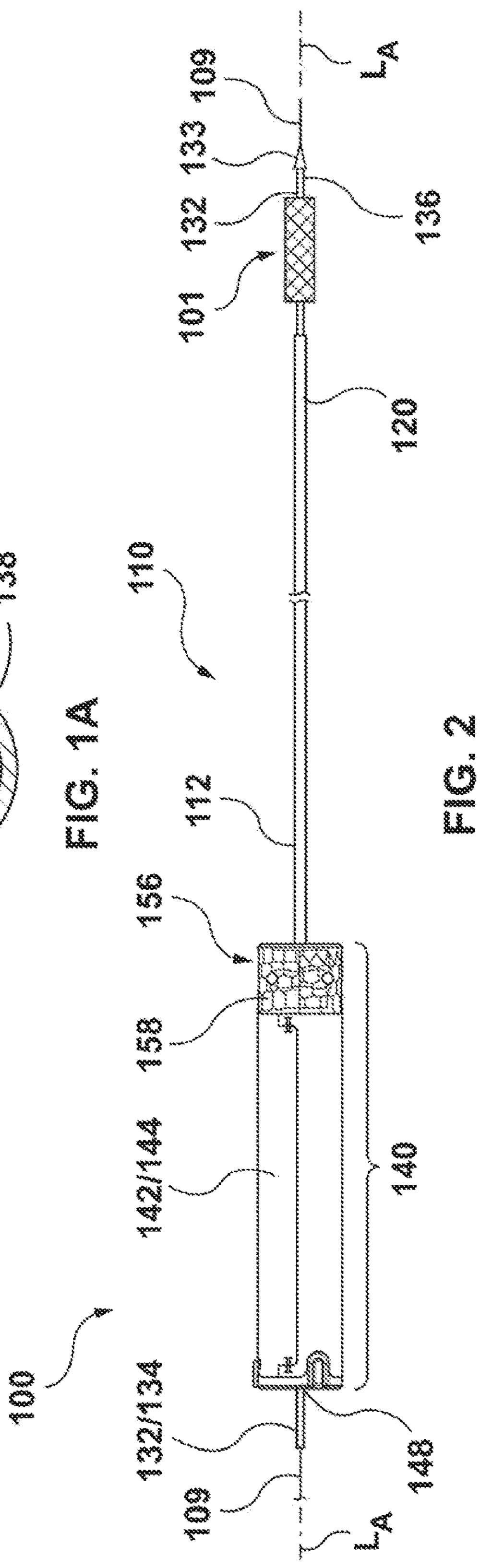
FIG. 2 is a side view of the delivery system of FIG. 1, wherein the delivery system is in a deployed configuration.
Figure 1B:
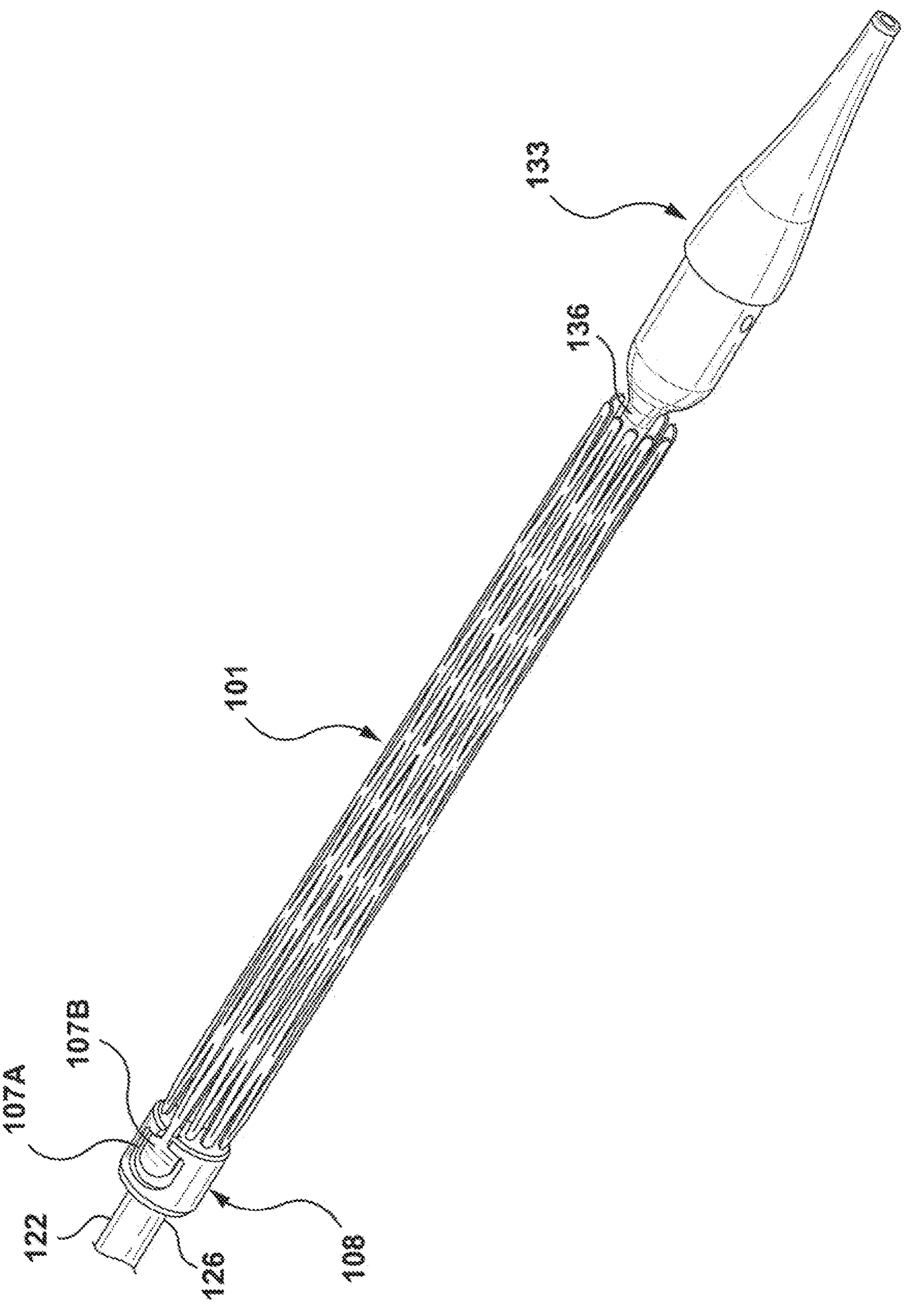
FIG. 1B is a perspective view of a distal portion of the delivery system of FIG. 1, wherein the delivery system is in the delivery configuration and an outer sheath of the delivery system is not shown for illustrative purposes only.

The delivery system will be described in more detail with reference to the figures. A delivery system 100 includes a self-expanding prosthesis 101 configured to foreshorten during deployment thereof and a delivery device 110 configured to percutaneously deliver the self-expanding prosthesis 101. More particularly, the delivery system 100 is shown in FIGS. 1, 1A, 1B, and 2. FIG. 1 is a side view of the delivery system 100, with an outer sheath 112 thereof shown in a delivery configuration in which the outer sheath 112 surrounds and constrains the self-expanding prosthesis 101 (not shown in FIG. 1A) in a compressed or delivery configuration. FIG. 1A is a cross-sectional view taken along line A-A of FIG. 1A. FIG. 1B is a perspective view of a distal portion of the delivery system 100 in the delivery configuration but with the outer sheath 112 not shown for illustrative purposes only. FIG. 2 is a side view of the delivery system 100 after the outer sheath 112 has been retracted to allow the prosthesis 101 to self-expand to a deployed or expanded configuration. The delivery device 110 includes a handle 140 having an actuator 142 thereon. The components of the handle 140 will be described in detail herein with respect to FIGS. 7-14.

In addition to the outer sheath 112 operatively coupled to the handle 140, the delivery device 110 further includes a pusher shaft 122 slidingly disposed within the outer sheath 112 and operatively coupled to the handle 140, and an inner shaft 132 disposed within the pusher shaft 122. The outer sheath 112, the pusher shaft 122, and the inner shaft 132 each distally extend from within the handle 140. As will be explained in greater detail herein, the outer sheath 112 and the pusher shaft 122 are configured to simultaneously move or translate in opposing axial directions along a central longitudinal axis LA of the delivery device 110 via actuation of the actuator 142 on the handle 140 to compensate for the foreshortening of the self-expanding prosthesis 101 during deployment. Stated another way, to deploy the self-expanding prosthesis 101, the outer sheath 112 is proximally retracted to expose the self-expanding prosthesis 101 and the pusher shaft 122 is simultaneously distally advanced to push the self-expanding prosthesis 101. The outer sheath 112 and the pusher shaft 122 are configured to move at different rates such that the pusher shaft 122 is configured to distally advance a predetermined distance that compensates for foreshortening of the self-expanding prosthesis 101.

The outer sheath 112 has a proximal end 114 disposed within the handle 140 and a distal end 116. As best shown in FIG. 1A, the outer sheath 112 defines a lumen 118 and is slidingly and concentrically disposed over the pusher shaft 122. A distal portion of the outer sheath 112 defines a capsule 120. The capsule 120 is configured to retain the self-expanding prosthesis 101 in a collapsed configuration for delivery to the desired treatment location as will be described in more detail herein. While the capsule 120 is described herein as a distal portion of the outer sheath 112, the capsule 120 may be a separate component coupled to the distal end of the outer sheath 112. Moreover, although the outer sheath 112 is described herein as a single component, this is not meant to limit the design, and the outer sheath 112 may include components such as, but not limited to a proximal shaft or other components suitable for the purposes described herein.

The pusher shaft 122 has a proximal end 124 disposed within the handle 140 and a distal end 126 disposed inside of the outer sheath 112 when the outer sheath 112 is disposed over the self-expanding prosthesis 101. The distal end 126 of the pusher shaft 122 includes a spindle 108 which is releasably coupled to an end of the self-expanding prosthesis 101 such that the self-expanding prosthesis axially moves with the pusher shaft 122. As best shown on the perspective view of FIG. 1B, having the outer sheath 112 removed for illustrative purposes only, the spindle 108 is a tubular component having at least one recess 107A formed on an outer surface thereof that is configured to receive a paddle 107B extending proximally from the self-expanding prosthesis 101. The paddle 107B fits within or mates with the recess 107A of the spindle 108 such that the self-expanding prosthesis 101 axially moves concurrently with the pusher shaft 122. Although only one recess 107A is visible on FIG. 1B, it will be understood by one of ordinary skill in the art that the spindle 108 may include two or more recesses for receiving a mating paddle of the self-expanding prosthesis 101, such as for example first and second recesses at opposing locations on the spindle 108. As best shown in FIG. 1A, the pusher shaft 122 defines a lumen 128 and is concentrically disposed over the inner shaft 132. The inner shaft 132 has a proximal end 134 proximally extending from the handle 140 and a distal end 136. A tapered flexible nosecone or distal tip 133 may be coupled to the distal end 136 of the inner shaft 132 as shown in FIG. 1 and FIG. 2. As best shown in FIG. 1A, the inner shaft 132 defines a lumen 138 such that the delivery system 100 may be slidingly disposed and tracked over a guidewire 109. The inner shaft 132 may be coupled to the pusher shaft 122 at the spindle 108 such that the inner shaft 132 and the pusher shaft 122 axially move as an assembly.

The inner shaft 132 is configured to receive the self-expanding prosthesis 101 on a distal portion thereof and the outer sheath 112 is configured to compressively retain the self-expanding prosthesis 101 on the distal portion of the inner shaft 132 during delivery, as shown in FIG. 1. Stated another way, the outer sheath 112 surrounds and constrains the self-expanding prosthesis 101 in a compressed or delivery configuration. As previously described, the distal end 126 of the pusher shaft 122 includes the spindle 108 to which the self-expanding prosthesis 101 is releasably coupled. The self-expanding prosthesis 101 axially moves with the pusher shaft 122. The self-expanding prosthesis 101 is shown in the view of FIG. 2 but is obscured from view by the outer sheath 112 in FIG. 1. During deployment of the self-expanding prosthesis 101 in situ, the outer sheath 112 is proximally retracted with respect to the prosthesis 101, thereby incrementally exposing the self-expanding prosthesis 101 until the self-expanding prosthesis 101 is fully exposed and thereby released from the delivery device 110. More particularly, when the outer sheath 112 is proximally retracted beyond the spindle 108, the paddles 107B of the self-expanding prosthesis 101 are no longer held within the recesses 107A of the spindle and the self-expanding prosthesis 101 is permitted to self-expand to its deployed configuration.

Figure 3:
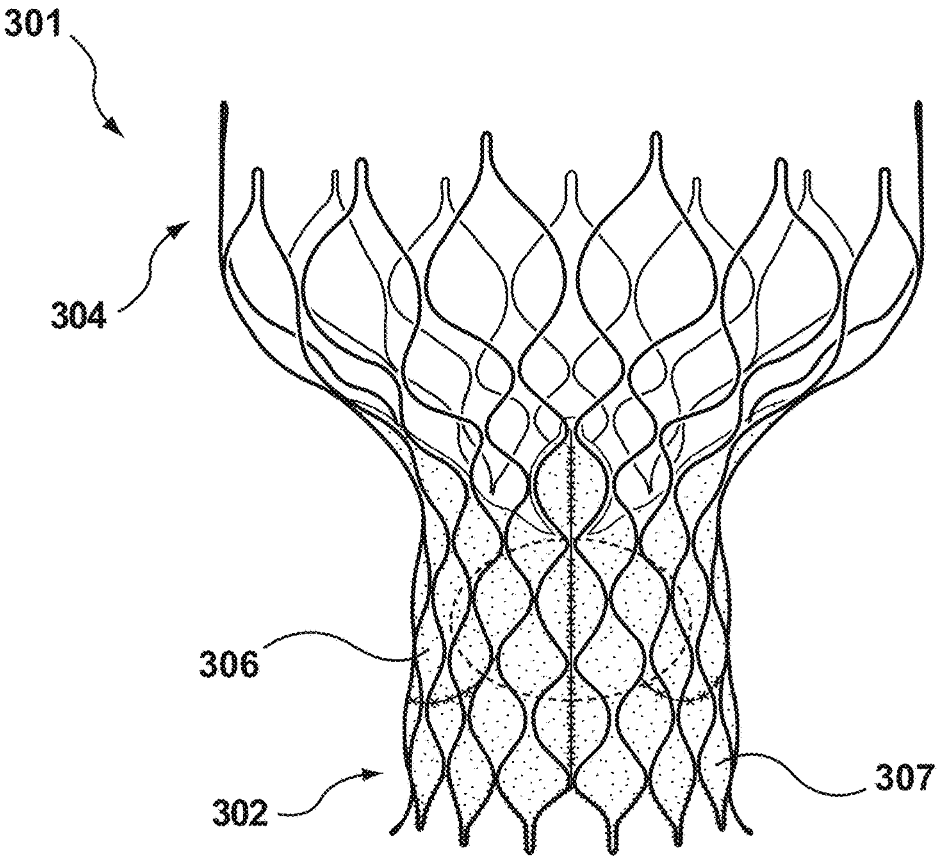
FIG. 3 is a side perspective view of a heart valve prostheses for use in embodiments hereof.
Figure 4:
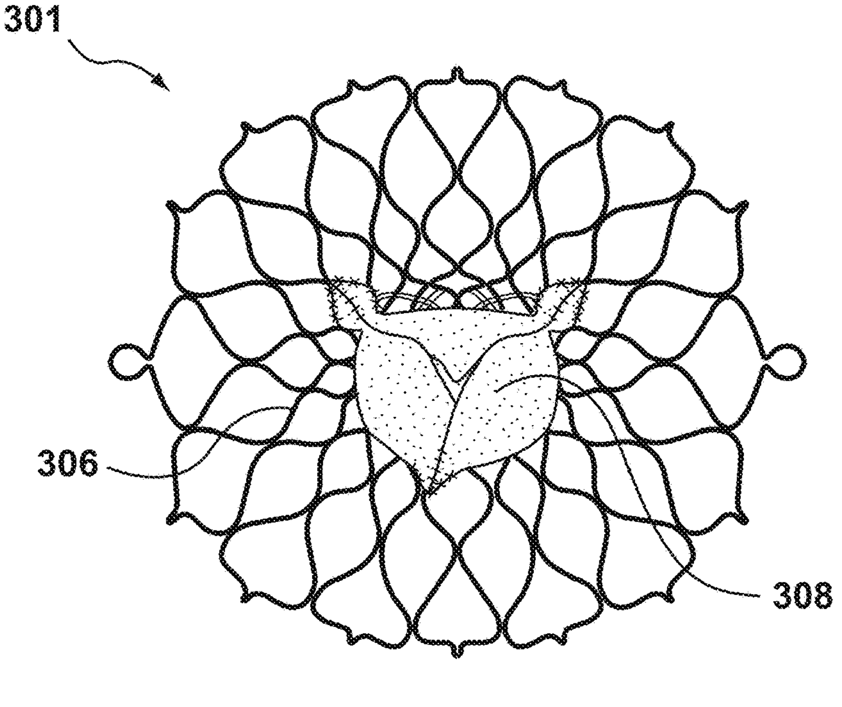
FIG. 4 is an end view of the heart valve prosthesis of FIG. 3.

FIG. 3 and FIG. 4 illustrate side perspective and end views, respectively, of a heart valve prosthesis 301 that may be utilized as the self-expanding prosthesis 101 according to an embodiment hereof. The heart valve prosthesis 301 is merely exemplary and is described in more detail in U.S. Patent Application Pub. No. 2011/0172765 to Nguyen et al., which is herein incorporated by reference in its entirety. It is understood that any number of alternate heart valve prostheses can be used with the delivery devices and methods described herein. In addition, the delivery device 110 may also be used with other self-expanding prostheses such as stent-graft prostheses, uncovered stents, bare metal stents, drug eluting stents, and any self-expanding structure that is configured to foreshorten during deployment.

Heart valve prosthesis 301 includes an expandable stent or frame 306 that supports a prosthetic valve component 308 within the interior of the frame 306. In embodiments hereof, the frame 306 is self-expanding to return to an expanded state from a compressed or constricted delivery state. In the embodiment depicted in FIGS. 3 and 4, the frame 306 has an expanded, longitudinally asymmetric hourglass configuration including a first end or portion 302 and a relatively enlarged second end or portion 304. Each portion of frame 306 may be designed with a number of different configurations and sizes to meet the different requirements of the location in which it may be implanted. When configured as a replacement for an aortic valve, as shown for example in FIGS. 15-17 described in more detail herein, the first end 302 functions as an inflow end of the heart valve prosthesis 301 and extends into and anchors within the aortic annulus of a patient's left ventricle, while the enlarged second end 304 functions as an outflow end of the heart valve prosthesis 301 and is positioned in the patient's ascending aorta. When configured as a replacement for a mitral valve, the enlarged second end 304 functions as an inflow end of the heart valve prosthesis 301 and is positioned in the patient's left atrium, while the first end 302 functions as an outflow end of the heart valve prosthesis 301 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each portion of the frame 306 may have the same or different cross-portion which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed asymmetric hourglass configuration of FIGS. 3 and 4, the frame 306 may have a symmetric hourglass configuration, a generally tubular configuration, or other stent configuration or shape known in the art for valve replacement.

As previously mentioned, the heart valve prosthesis 301 includes the prosthetic valve component 308 within the interior of frame 306. The prosthetic valve component 308 is capable of blocking flow in one direction to regulate flow there through via valve leaflets that may form a bicuspid or tricuspid replacement valve. FIG. 4 is an end view of FIG. 3 and illustrates an exemplary tricuspid valve having three leaflets, although a bicuspid leaflet configuration may alternatively be used in embodiments hereof. More particularly, if the heart valve prosthesis 301 is configured for placement within a native valve having three leaflets such as the aortic, tricuspid, or pulmonary valves, the heart valve prosthesis 301 may include three valve leaflets. If the heart valve prosthesis 301 is configured for placement within a native valve having two leaflets such as the mitral valve, the heart valve prosthesis 301 may include two valve leaflets. Valve leaflets are sutured or otherwise securely and sealingly attached to the interior surface of the frame 306 and/or graft material 307 which encloses or lines the frame 306 as would be known to one of ordinary skill in the art of prosthetic tissue valve construction. Leaflets are attached along their bases to the graft material 307, for example, using sutures or a suitable biocompatible adhesive. Adjoining pairs of leaflets are attached to one another at their lateral ends to form commissures. The orientation of the leaflets within the frame 306 would change depending on which end of the heart valve prosthesis 301 is the inflow end and which end of the heart valve prosthesis 301 is the outflow end, thereby ensuring one-way flow of blood through the heart valve prosthesis 301.

Leaflets may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

The graft material 307 may also be a natural or biological material such as pericardium or another membranous tissue such as intestinal submucosa. Alternatively, the graft material 307 may be a low-porosity woven fabric, such as polyester, Dacron fabric, or PTFE, which creates a one-way fluid passage when attached to the stent. In one embodiment, the graft material 307 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side.

These and other appropriate cardiovascular fabrics are commercially available from Bard Peripheral Vascular, Inc. of Tempe, Ariz., for example.

The heart valve prosthesis 301 is designed or configured to have a specific amount of foreshortening or contraction which reduces the length thereof upon radial expansion. Upon radial expansion of the heart valve prosthesis 301, the heart valve prosthesis 301 increases in diameter and decreases in length. Stated another way, the heart valve prosthesis 301 is configured to foreshorten as the heart valve prosthesis 301 transitions between a delivery or compressed configuration to a deployed or expanded configuration.

Figures 5A, 5B:
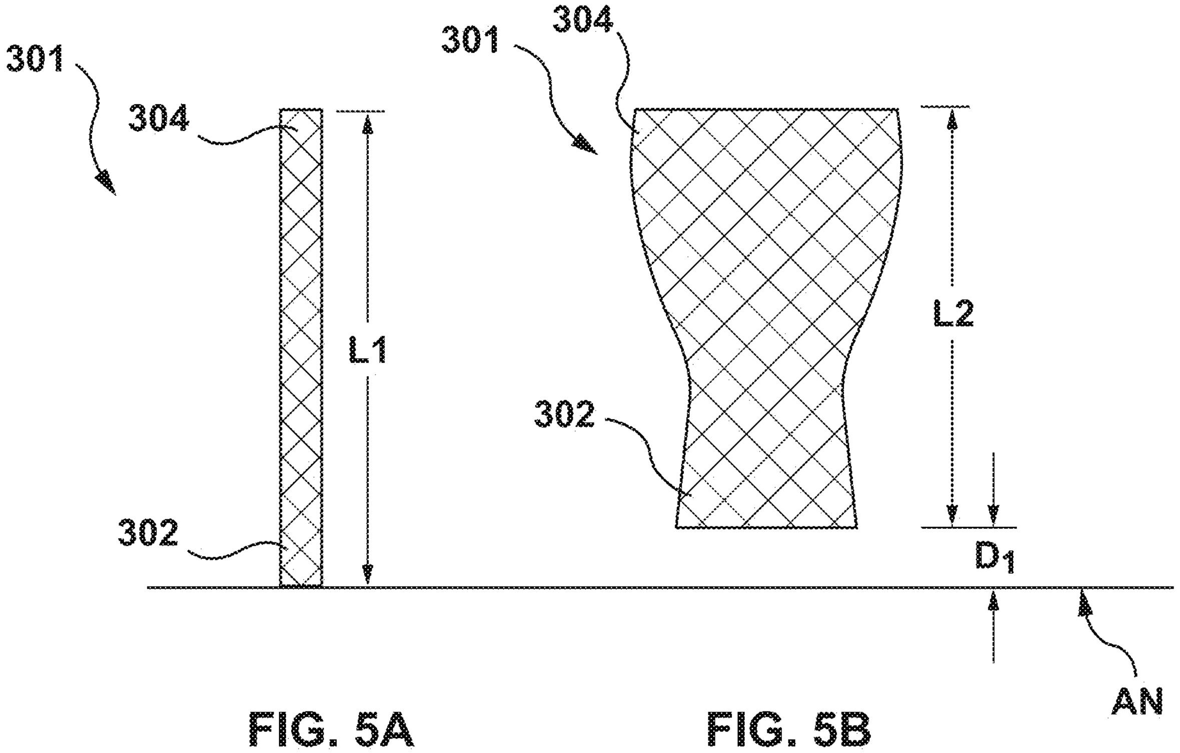
FIG. 5A is a side view illustration of the heart valve prosthesis of FIG. 3 in a delivery or compressed configuration, wherein the proximal or inflow end of the heart valve prosthesis is aligned along a plane of a native valve annulus.
FIG. 5B is a side view illustration of the heart valve prosthesis of FIG. 3 in a deployed or expanded configuration, wherein the proximal or inflow end of the heart valve prosthesis is spaced apart from a plane of a native valve annulus.

FIGS. 5A-5B illustrate the shifting or movement in situ of the heart valve prosthesis 301 when deployed using a standard delivery system that does not compensate for foreshortening. In FIGS. 5A-5B, a plane representing the native annulus AN is depicted adjacent to the first or inflow end 302 of the heart valve prosthesis 301. FIG. 5A is a side view illustration of the heart valve prosthesis 301 in a delivery or compressed configuration, with the first or inflow end 302 shown aligned with or positioned at the native annulus AN. Although the heart valve prosthesis 301 is shown removed from a delivery device for illustrative purposes only, it will be understood that at this stage of deployment an outer sheath of a standard delivery system is disposed over the entire length of the heart valve prosthesis 301 and constrains or compresses the heart valve prosthesis 301 into the delivery or compressed configuration.

FIG. 5B is a side view illustration of the heart valve prosthesis 301 in its deployed or expanded configuration after the outer sheath of the standard delivery system is fully proximally retracted to expose the entire length of the heart valve prosthesis 301. As the heart valve prosthesis 301 deploys, as shown on FIG. 5B, it foreshortens or contacts from a first length L1 to a second length L2 and as a result of the foreshortening, the first or inflow end 302 of the heart valve prosthesis 301 moves away from the native annulus AN such that the heart valve prosthesis 301 is spaced apart from its target location by a distance of D1.

The delivery device 110 is configured to compensate for the foreshortening of the heart valve prosthesis 301 such that the first or inflow end 302 is accurately positioned at the native annulus AN. More particularly, distal advancement or movement of the pusher shaft 122 during deployment of the heart valve prosthesis 301 ensures that the first or inflow end 302 of the heart valve prosthesis 301 remains positioned at the native annulus AN during deployment. In an embodiment, the heart valve prosthesis 301 is configured to foreshorten the distance of D1 during deployment thereof and the pusher shaft 122 (the distal end of which is releasably coupled to the heart valve prosthesis 301) is configured to distally advance the heart valve prosthesis 301 the same amount, i.e., the distance of D1, during deployment. For example, the heart valve prosthesis 301 may be configured to foreshorten a distance of 8 mm during deployment thereof and the pusher shaft 122 is then configured to distally advance the heart valve prosthesis 301 the distance of 8 mm during deployment to compensate for the foreshortening of the heart valve prosthesis 301.

Figures 6A, 6B:
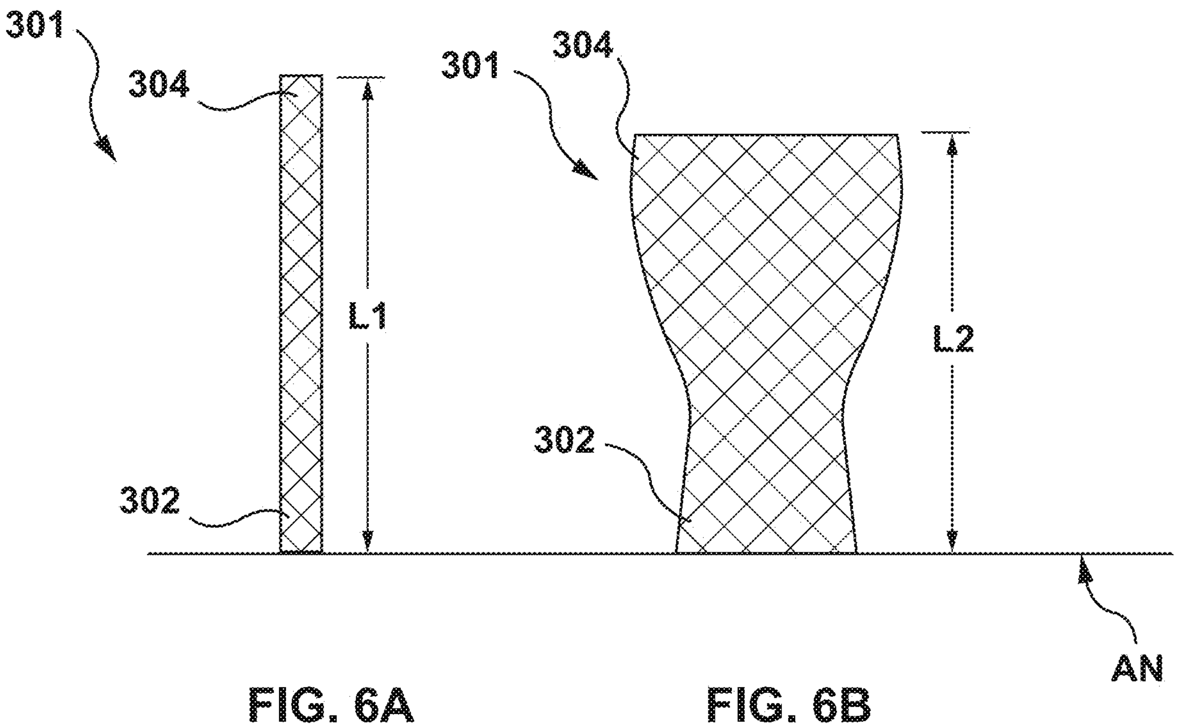
FIG. 6A is a side view illustration of the heart valve prosthesis of FIG. 3 in the delivery or compressed configuration, wherein the proximal or inflow end of the heart valve prosthesis is aligned along a plane of a native valve annulus.
FIG. 6B is a side view illustration of the heart valve prosthesis of FIG. 3 in the deployed or expanded configuration, wherein the proximal or inflow end of the heart valve prosthesis remains aligned along a plane of a native valve annulus.

FIGS. 6A-6B illustrate the transition of the heart valve prosthesis 301 when deployed using the delivery device 110 that is configured to compensate for foreshortening of the heart valve prosthesis 301. In FIGS. 6A-6B, a plane representing the native annulus AN is depicted adjacent to the first or inflow end 302 of the heart valve prosthesis 301. FIG. 6A is a side view illustration of the heart valve prosthesis 301 in a delivery or compressed configuration, with the first or inflow end 302 shown aligned with or positioned at the native annulus AN. Although the heart valve prosthesis 301 is shown removed from the delivery device 110 for illustrative purposes only, it will be understood that at this stage of deployment the outer sheath 112 of the delivery device 110 is disposed over the entire length of the heart valve prosthesis 301 and constrains or compresses the heart valve prosthesis 301 into the delivery or compressed configuration.

FIG. 6B is a side view illustration of the heart valve prosthesis 301 in a deployed or expanded configuration after the outer sheath 112 of the delivery device 110 is fully proximally retracted to expose the entire length of the heart valve prosthesis 301. As the heart valve prosthesis 301 deploys, as shown on FIG. 6B, it foreshortens or contacts from a first length L1 to a second length L2. However, due to the distal advancement of the pusher shaft 122, the first or inflow end 302 of the heart valve prosthesis 301 remains aligned or positioned at the native annulus AN as shown in FIG. 6B.

Figure 7:
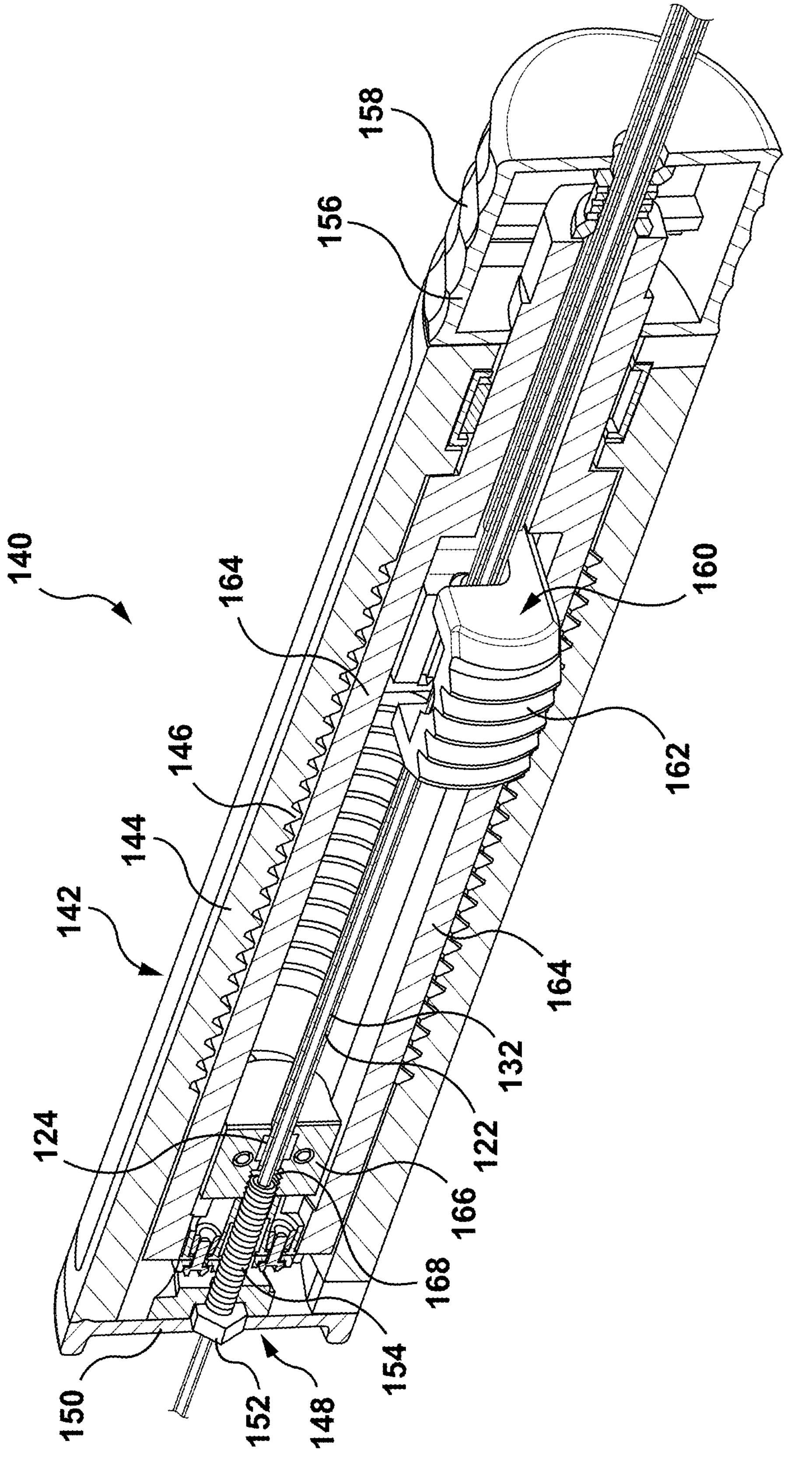
FIG. 7 is an enlarged cut-away view of a handle of the delivery system of FIG. 1.
Figure 8:
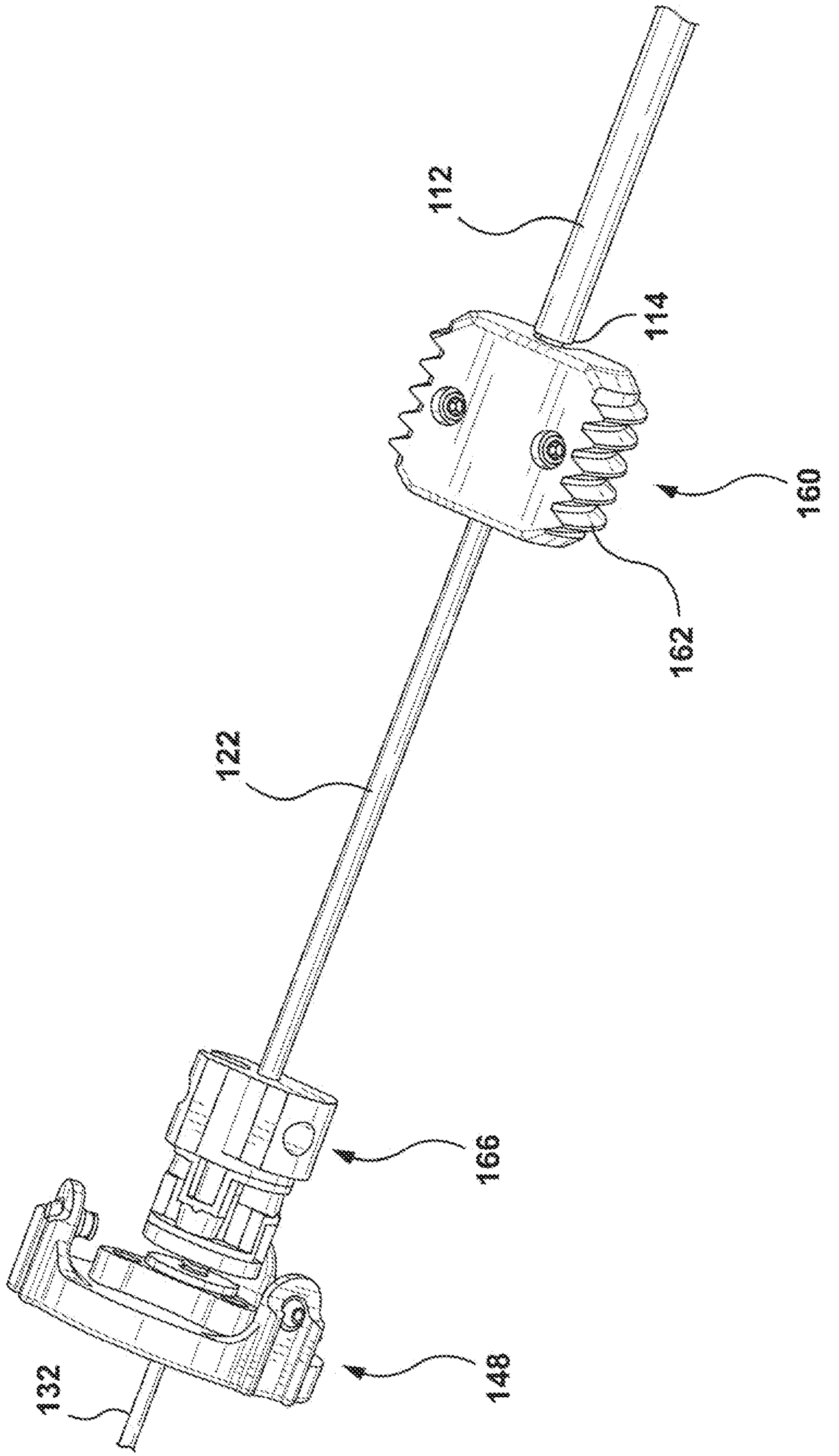
FIG. 8 is a perspective view of internal components of the handle of the delivery system of FIG. 1, wherein the internal components are removed from the handle for illustrative purposes only.

Turning to FIGS. 7 and 8, the handle 140 will now be described in more detail. FIG. 7 is an enlarged cut-away view of the handle 140, while FIG. 8 is a perspective view of some of the internal components of the handle 140. The handle 140 includes the actuator 142, a cap assembly 148 having a screw 152, a stationary grip 156, a stationary frame 164, a first carriage 160 attached to the proximal end 114 of the outer sheath 112, and a second carriage 166 attached to the proximal end 124 of the pusher shaft 122. The inner shaft 132 is disposed through the pusher shaft 122 and through a lumen of the screw 152, with the proximal end 134 thereof proximally extending outside of the handle 140. As described above, although not shown on FIG. 7, the guidewire 109 may be slidingly disposed through the inner shaft 132.

The actuator 142 is shown in FIG. 7 as a rotatable housing or shell 144, but may have an alternative configuration as may be understood by one of ordinary skill in the art. The handle 140 is configured such that actuation of the actuator 142 in a first direction results in the outer sheath 112 being proximally retracted and the pusher shaft 122 being simultaneously distally advanced. Stated another way, when the rotatable housing 144 is rotated in a first or clockwise direction, the outer sheath 112 proximally retracts and the pusher shaft 122 simultaneously distally advances. Actuation of the actuator 142 in a second or opposing direction results in the outer sheath 112 being distally advanced and the pusher shaft 122 being proximally retracted. Stated another way, when the rotatable housing 144 is rotated in a second or counter-clockwise direction, the outer sheath 112 distally advances and the pusher shaft 122 simultaneously proximally retracts.

As best shown in FIG. 7, the rotatable housing 144 is a generally tubular structure provided with a threaded interior wall, i.e., a second set of threads 146 are formed or disposed on an interior surface thereof which will be described in more detail below. The stationary frame 164 is a generally tubular structure that is disposed within the rotatable housing 144 and is further fixed or attached to the stationary grip 156 disposed at a distal end of the handle 140. The stationary grip 156 may include a textured outer surface 158 and is configured to be held stationary by the clinician during rotation of the rotatable housing 144 and operation of the handle 140. Similarly, the stationary frame 164 is fixedly attached to the stationary grip 156 and remains stationary during rotation of the rotatable housing 144 and operation of the handle 140.

Figure 9:
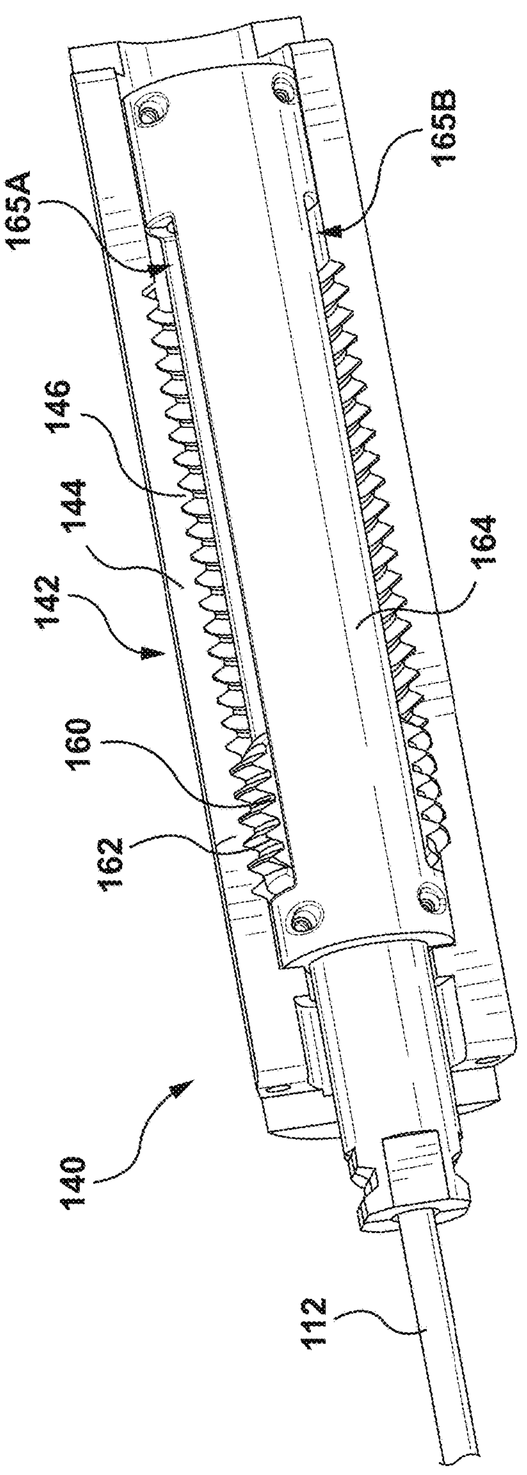
FIG. 9 is another enlarged cut-away view of the handle of the delivery system of FIG. 1.
Figure 11:
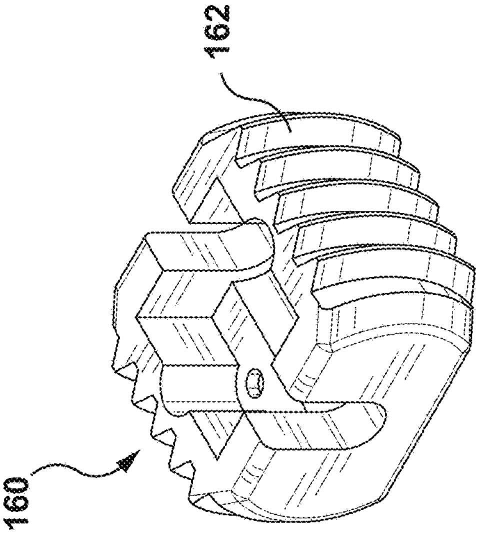
FIG. 11 is a perspective view of the first carriage of the handle of the delivery system of FIG. 1, wherein the first carriage is removed from the handle for illustrative purposes only.
Figure 10:
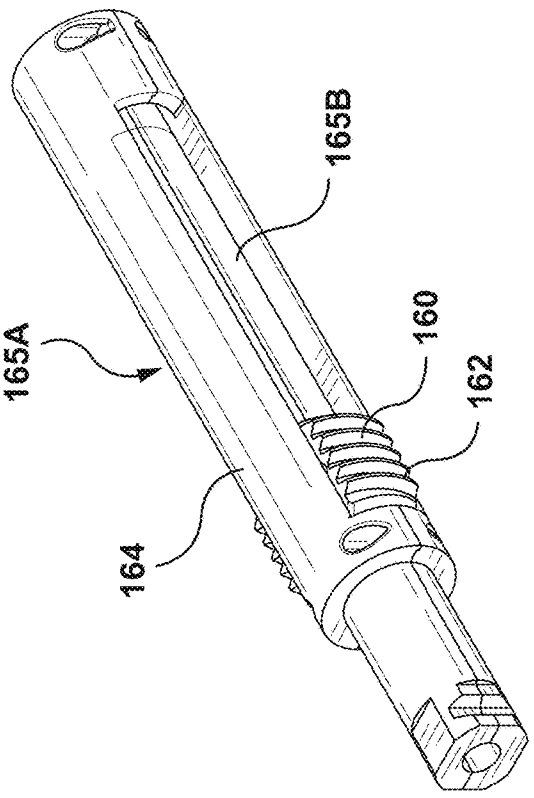
FIG. 10 is a perspective view of a first carriage and a stationary frame of the handle of the delivery system of FIG. 1, wherein the first carriage and the stationary frame are removed from the handle for illustrative purposes only.

Interaction between the handle 140 and the outer sheath 112 will be described in more detail with additional reference to FIGS. 9-11. FIG. 9 is another enlarged cut-away view of the handle 140 while FIG. 10 is a perspective view showing the first carriage 160 and the stationary frame 164 removed from the handle 140 for illustrative purposes. FIG. 11 is a perspective view of only the first carriage 160 removed from the handle 140 for illustrative purposes. The proximal end 114 of the outer sheath 112 is disposed within and fixedly attached to the first carriage 160 such that the outer sheath 112 axially moves with the first carriage 160, which is disposed within the stationary frame 164. The first carriage 160 includes a first set of threads 162 on an external surface thereof that are configured to mate with the second set of threads 146 on an internal surface of the rotatable housing 144. Due to the threaded relationship between the first carriage 160 and the rotatable housing 144, and also due to the first carriage 160 being prevented from rotating as described in more detail below, the outer sheath 112 longitudinally translates with the first carriage 160 when the rotatable housing 144 is rotated.

More particularly, as best shown in FIGS. 9-11, the first carriage 160 is provided with a threaded exterior wall, i.e., the first set of threads 162 on an exterior surface thereof. The threaded exterior wall of the first carriage 160 extends through two opposing slots 165A, 165B of the stationary frame 164. Each slot 165A, 165B is a slot, channel, gap, window, or opening formed in or through a sidewall of the stationary frame 164. As such, the first set of threads 162 on the first carriage 160 extend or are positioned through the opposing slots 165A, 165B of the stationary frame 164 and mate with the second set of threads 146 on an interior surface of the rotatable housing 144. Further, with the first carriage 160 disposed within the stationary frame 164 and the first set of threads 162 on the first carriage 160 extending or positioned through the opposing slots 165A, 165B of the stationary frame 164, the first carriage 160 is prevented from rotating with the rotatable housing 144. Stated another way, the walls of each slot 165A, 165B of the stationary frame 164 are disposed adjacent to each side of first set of threads 162 on the first carriage 160 to prevent rotation of the first carriage 160.

When the rotatable housing 144 is rotated, the rotatable housing 144 does not axially move due to mechanical engagement with the stationary grip 156 and the stationary frame 164 attached thereto. More particularly, the stationary grip 156 and the stationary frame 164 attached thereto are configured to remain stationary during rotation of the rotatable housing 144 and operation of the handle 140. When the rotatable housing 144 is rotated, the rotatable housing 144 spins without translating or moving axially because the rotatable housing 144 abuts against the stationary grip 156 and the stationary frame 164 attached thereto.

When the rotatable housing 144 rotates, the thread engagement between the first set of threads 162 of the first carriage 160 and the second set of threads 146 of the rotatable housing 144 cause axial movement or translation of the first carriage 160 and the outer sheath 112 attached thereto. Threads 146, 162 are used to convert rotational to translational or linear movement. More particularly, because the first carriage 160 is prevented from rotating therewith due to engagement with the walls of each slot 165A, 165B of the stationary frame 164 as described above, and because the rotatable housing 144 does not axially move due to the stationary grip 156 and the stationary frame 164 attached thereto, the rotational movement of the rotatable housing 144 and the first carriage 160 is converted to translational or linear movement of the first carriage 160 due to the threaded relationship between the first carriage 160 and the rotatable housing 144.

Figure 13:
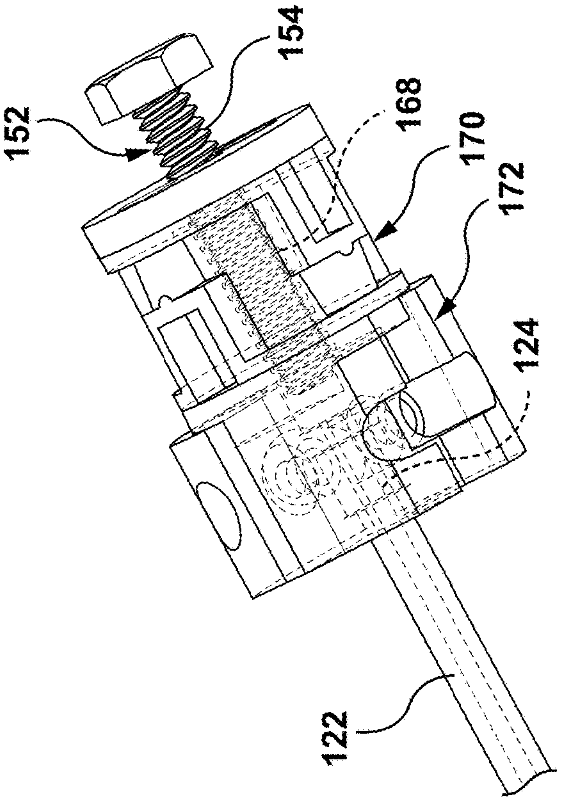
FIG. 13 is a perspective view of internal components of the handle of the delivery system of FIG. 1, wherein the internal components are removed from the handle for illustrative purposes only and some of the internal components are shown in phantom for illustrative purposes only.
Figure 14:
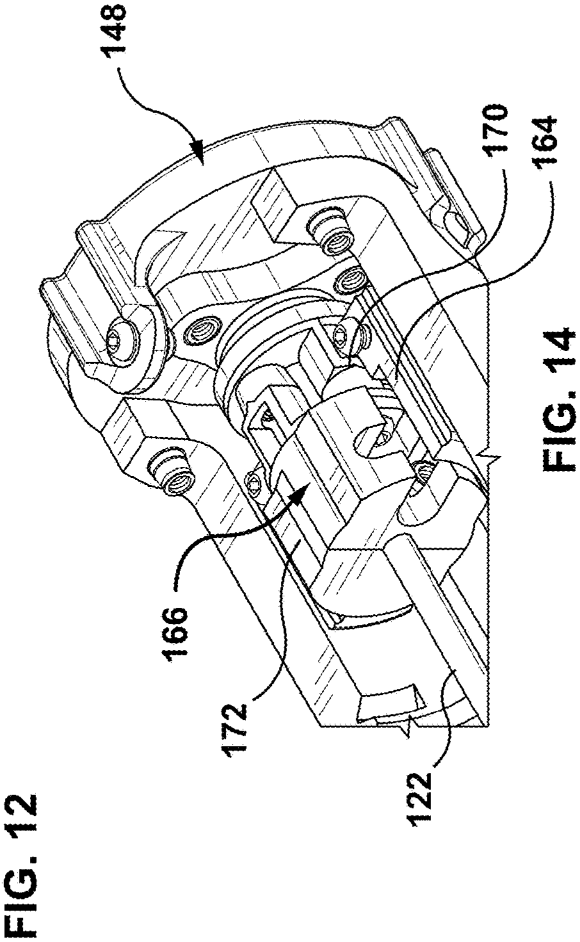
FIG. 14 is another enlarged cut-away view of the handle of the delivery system of FIG. 1.
Figure 12:
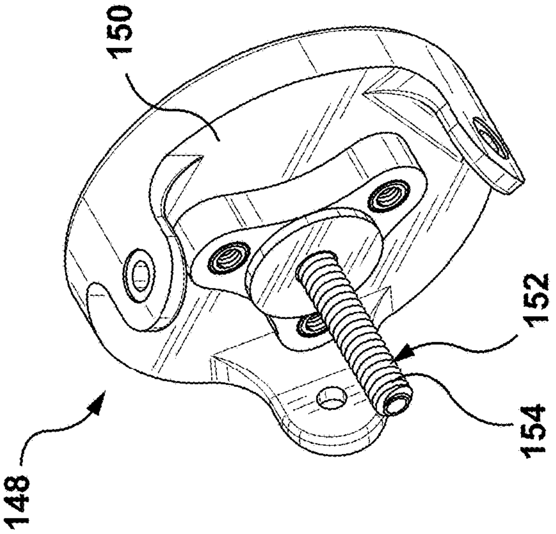
FIG. 12 is a perspective view of a cap assembly of the handle of the delivery system of FIG. 1, wherein the cap assembly is removed from the handle for illustrative purposes only.

Interaction between the handle 140 and the pusher shaft 122 will be described in more detail with additional reference to FIGS. 12-14. FIG. 12 is a perspective view of the cap assembly 148 removed from the handle 140 for illustrative purposes only, while FIG. 13 is a perspective view showing the second carriage 166 and the cap assembly 148 removed from the handle 140 for illustrative purposes. FIG. 14 is an enlarged cut away view of a portion of the handle 140, illustrating the interaction between the second carriage 166 and the stationary frame 164. The proximal end 124 of the pusher shaft 122 is attached to the second carriage 166 which is disposed within the stationary frame 164. The second carriage 166 includes a third set of threads 168 on an internal surface thereof that are configured to mate with a fourth set of threads 154 on an external surface of the screw 152 of the cap assembly 148. Due to the threaded relationship between the second carriage 166 and the cap assembly 148, the pusher shaft 122 longitudinally translates with the second carriage 166 when the rotatable housing 144 is rotated by a clinician.

More particularly, referring to FIG. 12, the cap assembly 148 includes a cap 150 and the screw 152 having the fourth set of threads 154 formed on an external surface thereof. The cap assembly 148 forms the proximal end of the handle 140 and is fixedly attached to the rotatable housing 144 such that the cap assembly 148 rotates therewith. As shown in FIGS. 13 and 14, the second carriage 166 includes a second carriage bracket 170 and a second carriage retainer 172. The second carriage bracket 170 is provided with a threaded interior wall, i.e., the third set of threads 168 formed on an internal surface thereof. The third set of threads 168 are configured to mate with or engage the fourth set of threads 154 formed on the external surface of the screw 152. The second carriage retainer 172 is attached to the second carriage bracket 170 such that they move in an axial direction as an assembly. The second carriage retainer 172 is configured to receive and is fixedly attached to the proximal end 124 of the pusher shaft 122 such that the pusher shaft 122 axially moves with the second carriage retainer 172. Further, the second carriage retainer 172 is disposed within the stationary frame 164 and the shape thereof is configured to prevent the second carriage 166 from rotating with the screw 152. Stated another way, the second carriage retainer 172 has a non-circular cross-section that abuts against the internal walls of the stationary frame 164 to prevent rotation of the second carriage retainer 172 therein, and thereby similarly prevent rotation of the second carriage 166.

When the rotatable housing 144 is rotated, the cap assembly 148 having the screw 152 rotates therewith and the thread engagement between the third set of threads 168 of the second carriage 166 and the fourth set of threads 154 of the screw 152 cause axial movement or translation of the second carriage 166 and the pusher shaft 122 attached thereto. Threads 168, 154 are used to convert rotational to translational or linear movement. More particularly, because the second carriage 166 is prevented from rotating due to engagement of the second carriage retainer 172 with the internal walls of the stationary frame 164 as described above, the rotational movement of the rotatable housing 144/cap assembly 148 and the second carriage 166 is converted to translational or linear movement of the second carriage 166 due to the threaded relationship between the second carriage 166 and the screw 152 of the cap assembly 148.

Notably, the first set of threads 162 on the first carriage 160 are opposingly pitched (i.e., having a different handedness) to the third set of threads 168 on the second carriage 166 to provide axial translation of the outer sheath 112 and the pusher shaft 122 in opposing directions. Stated another way, the outer sheath 112 and the pusher shaft 122 are configured to translate axially in opposing directions since the first set of threads 162 on the first carriage 160 have an opposite pitch than the third set of threads 168 on the second carriage 166. In order for the outer sheath 112 and the pusher shaft 122 to move in opposing directions via rotation of a single actuator (i.e., the rotate housing 144), the mating threads 162, 146 are opposingly pitched (i.e., having a different handedness) to the mating threads 154, 168. When the rotatable housing 144 rotates, the thread engagement between the first set of threads 162 of the first carriage 160 and the second set of threads 146 of the rotatable housing 144, and the thread engagement between the third set of threads 168 of the second carriage and the fourth set of threads 154 of the screw 152 of the cap assembly 148, cause axial movement or translation of the outer sheath 112 and the pusher shaft 122 in opposing or opposite axial directions.

Further, the outer sheath 112 and the pusher shaft 122 are configured to simultaneously move in opposing axial directions at different rates, with the pusher shaft 122 being configured to move at a lower rate than the outer sheath 112. The engaged pairs of threads may include different pitches so that the first carriage 160 and the second carriage 166 move at different rates. More particularly, the first set of threads 162 on the first carriage 160 has a first pitch and the third set of threads 168 on the second carriage 166 has a second pitch. The first pitch of the first set of threads 162 is higher than the second pitch of the third set of threads 168 such that the pusher shaft 122 is configured to move or translate at a lower rate than the outer sheath 112. In an embodiment, the outer sheath 112 is configured to move at least 50% faster than the pusher shaft 122. Further, in an embodiment, the pusher shaft 122 is configured to advance at a rate profile that corresponds with a rate of foreshortening of the self-expanding prosthesis 101. As described above with respect to FIGS. 6A-6B, the self-expanding prosthesis 101 is configured to foreshorten the distance of D1 during deployment thereof and the pusher shaft 122 is configured to distally advance the self-expanding prosthesis 101 the same amount during deployment. The rate profile of the pusher shaft 122 may be configured such that the pusher shaft 122 distally advances the self-expanding prosthesis 101 the same amount that the self-expanding prosthesis 101 foreshortens while the rate profile of the outer sheath 112 may be configured to proximally retract the full length of the self-expanding prosthesis 101 to fully deploy the self-expanding prosthesis 101. Although the different rates of retraction of the outer sheath 112 and advancement of the pusher shaft 122 are described herein as being achieved by different pitches of the first set of threads 162 and third set of threads 168, this is not meant to be limiting, and other ways to achieve the different rates may also be used.

Figure 17:
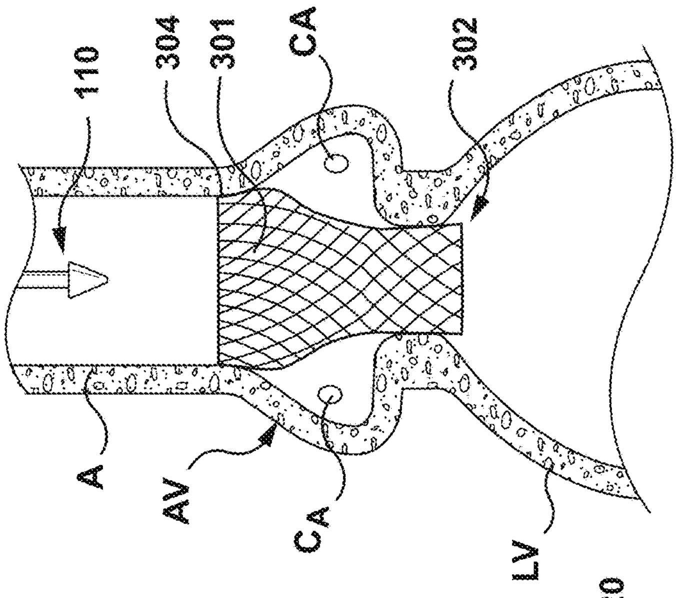
FIG. 17 illustrates a third step of a method of using the delivery system of FIG. 1 to deploy the heart valve prosthesis of FIG. 3, wherein the heart valve prosthesis is shown in the deployed or expanded configuration following deployment at the target treatment site.
Figure 16:
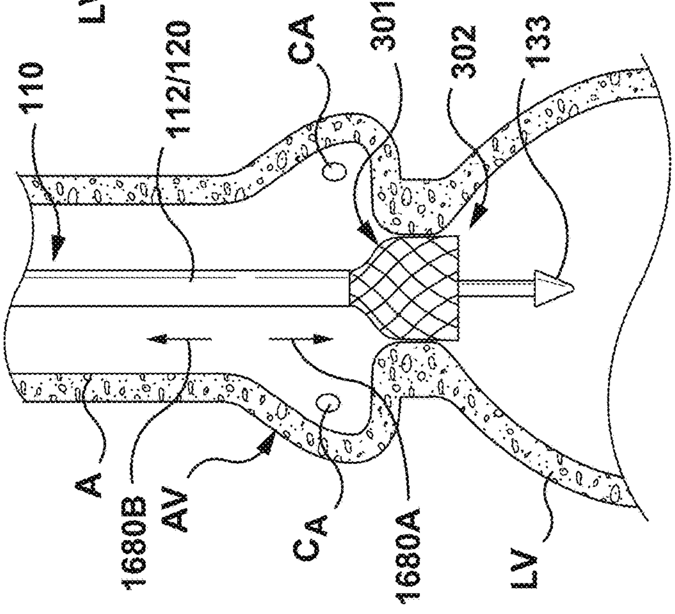
FIG. 16 illustrates a second step of a method of using the delivery system of FIG. 1 to deploy the heart valve prosthesis of FIG. 3, wherein the heart valve prosthesis is shown being transitioned from the delivery or compressed configuration to the deployed or expanded configuration at the target treatment site.
Figure 15:
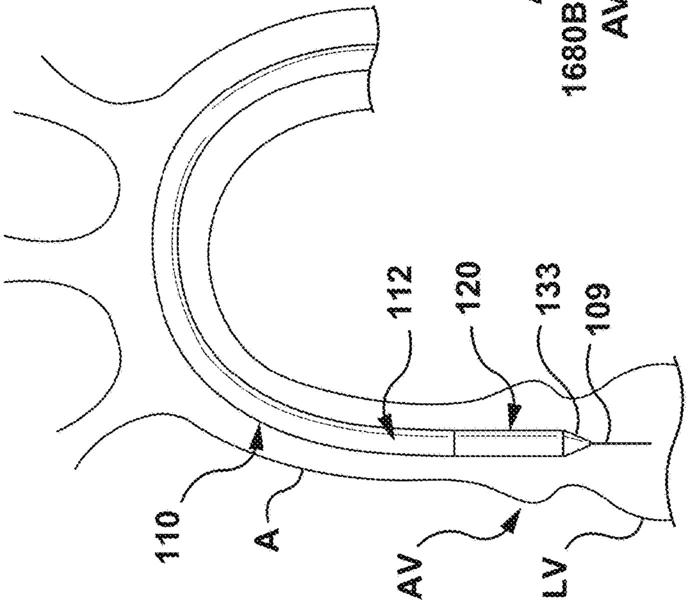
FIG. 15 illustrates a first step of a method of using the delivery system of FIG. 1 to deploy the heart valve prosthesis of FIG. 3, wherein the heart valve prosthesis is shown in the delivery or compressed configuration at the target treatment site.

A method of delivering and deploying the heart valve prosthesis 301 with the delivery device 110 is depicted in FIGS. 15-17. As shown in FIG. 15, in accordance with techniques known in the field of interventional cardiology and/or interventional radiology, the delivery system 100 including the delivery device 110 is transluminally advanced in a retrograde approach through the vasculature to the treatment site, which in this instance is a target diseased native aortic valve AV that extends between a patient's left ventricle LV and a patient's aorta A. Delivery of the delivery system 100 to the native aortic valve AV is accomplished via a percutaneous transfemoral approach in which the delivery system is tracked through the femoral artery, up the aorta and around the aortic arch in order to access the native aortic valve AV. The delivery system 100 may also be positioned within the desired area of the heart via different delivery methods known in the art for accessing heart valves. As shown, the delivery system 100 is tracked over the guidewire 109 that has previously been inserted into the patient vasculature. During delivery, as the heart valve prosthesis 301 is self-expanding, the heart valve prosthesis 301 remains compressed within the capsule 120 of the outer sheath 112 as the delivery system 100 is manipulated and navigated through the vasculature. The delivery system 100 is advanced until the distal tip 133 thereof is distal to the native aortic valve AV and disposed within the left ventricle LV as shown in FIG. 15, such that the first end 302 of the heart valve prosthesis 301 (which is the inflow and proximal end of the heart valve prosthesis 301 when the heart valve prosthesis 301 is configured for placement in a native aortic valve) is positioned at an annulus of a native aortic heart valve.

As shown in FIG. 16, which is a sectional view of the native aortic heart valve AV, the heart valve prosthesis 301 is deployed at the annulus of the native aortic heart valve AV and the heart valve prosthesis 301 foreshortens during deployment. During deployment of the heart valve prosthesis 301, the outer sheath 112 (and the capsule 120 forming the distal portion of the outer sheath 112) is proximally retracted and the pusher shaft 122 is simultaneously distally advanced. Because the distal end 126 of the pusher shaft 122 is releasably coupled to the heart valve prosthesis 301, distal advancement of the pusher shaft 122 pushes the heart valve prosthesis 301 in order to compensate for the foreshortening of the heart valve prosthesis 301. More particularly, the rotatable housing 144 (not shown in FIG. 16) is rotated in a first direction (i.e., clockwise) to cause the second carriage 166 to translate distally as represented by a directional arrow 1680A and the first carriage 160 to translate proximally as represented by a directional arrow 1680B. Movement of the first carriage 160 in a proximal direction as represented by the directional arrow 1680B causes the outer sheath 112 fixed thereto to move with the first carriage 160. Movement of the second carriage 166 in a distal direction as represented by the directional arrow 1680A causes the pusher shaft 122 fixed thereto to move with the second carriage 166. Thus, rotation of the rotatable housing 144 causes the outer sheath 112 to retract proximally while simultaneously causing the pusher shaft 122 to advance distally. Distal advancement of the pusher shaft 122 as the heart valve prosthesis 301 is deployed pushes the outflow or second end 304 of the heart valve prosthesis to 301 ensure that the inflow or first end 302 of the heart valve prosthesis 301 remains positioned at the annulus of the native aortic heart valve throughout deployment and further ensures that the inflow or first end 302 of the heart valve prosthesis 301 is positioned at the annulus of the native aortic heart valve after deployment is complete. When the outer sheath 112 is retracted such that all of the heart valve prosthesis 301 is uncovered, the heart valve prosthesis 301 is released from the pusher shaft 122, for example, by being released from the spindle 108 on the distal end 126 of the pusher shaft 122. As shown in FIG. 17, after deployment of the heart valve prosthesis 301 is complete, the delivery device 110 is then removed and the heart valve prosthesis 301 remains deployed within the native target heart valve.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A delivery device for percutaneously delivering a self-expanding prosthesis, the delivery device comprising:

a handle having an actuator thereon;

an outer sheath including a proximal end operatively coupled to the handle;

a pusher shaft slidingly disposed within the outer sheath, the pusher shaft having a proximal end operatively coupled to the handle; and an inner shaft disposed within the pusher shaft, the inner shaft having a proximal portion disposed within the handle and a distal portion configured to receive the self-expanding prosthesis thereon, wherein the inner shaft is coupled to the pusher shaft such that the inner shaft and the pusher shaft axially move together as an assembly relative to the outer sheath from a delivery orientation to a deployed orientation, wherein the outer sheath and the pusher shaft are configured to simultaneously move in opposing axial directions between the delivery orientation and the deployed orientation via actuation of the actuator on the handle.

2. The delivery device of claim 1, wherein the outer sheath and the pusher shaft are configured to simultaneously move in opposing axial directions at different rates, the pusher shaft being configured to move at a lower rate than the outer sheath.

3. The delivery device of claim 2, wherein the outer sheath is configured to move at least 50% faster than the pusher shaft.

4. The delivery device of claim 1, wherein actuation of the actuator in a first direction results in the outer sheath being proximally retracted and the pusher shaft being distally advanced and actuation of the actuator in a second direction results in the outer sheath being distally advanced and the pusher shaft being proximally retracted.

5. The delivery device of claim 1, wherein the actuator is a rotatable housing of the handle.

6. The delivery device of claim 5, wherein the proximal end of the outer sheath is attached to a first carriage disposed within the rotatable housing of the handle such that the outer sheath longitudinally translates with the first carriage, the first carriage comprising a first set of threads on an external surface thereof that are configured to mate with a second set of threads on an internal surface of the rotatable housing.

7. The delivery device of claim 6, wherein the proximal end of the pusher shaft is attached to a second carriage disposed within the rotatable housing of the handle such that the pusher shaft longitudinally translates with the second carriage, the second carriage comprising a third set of threads on an internal surface thereof that are configured to mate with a fourth set of threads on an external surface of a cap assembly that is configured to rotate with the rotatable housing.

8. The delivery device of claim 7, wherein the first set of threads and the third set of threads comprise opposite pitch directions.

9. The delivery device of claim 8, wherein the first set of threads has a first pitch and the third set of threads has a second pitch, the first pitch being higher than the second pitch.

10. The delivery device of claim 1, wherein a distal end of the distal portion of the inner shaft provided with a distal tip.

11. The delivery device of claim 10, wherein the distal portion of the inner shaft is disposed within the outer sheath and the distal tip engages and is distal to a distal end of the outer sheath in the delivery orientation, and the distal portion of the inner shaft is disposed outside of the outer sheath and the distal tip is distally spaced away from the distal end of the outer sheath in the deployed orientation.

12. A system comprising:

a self-expanding prosthesis configured to foreshorten during deployment thereof;

a delivery device configured to percutaneously deliver the self-expanding prosthesis, the delivery device comprising:

a handle comprising an actuator;

an outer sheath comprising a proximal end coupled to the handle;

a pusher shaft slidingly disposed within the outer sheath, the pusher shaft comprising a proximal end coupled to the handle and a distal end configured to releasably couple to the self-expanding prosthesis such that the self-expanding prosthesis axially moves therewith when coupled thereto, an inner shaft disposed within the pusher shaft and coupled to the pusher shaft, wherein the self-expanding prosthesis is disposed on a distal portion of the inner shaft during delivery thereof, a distal end of the distal portion of the inner shaft provided with a distal tip, wherein the distal tip, the inner shaft, and the pusher shaft are configured to axially move together as an assembly from a delivery orientation to a deployed orientation, wherein the distal portion of the inner shaft is disposed within the outer sheath and the distal tip engages and is distal to a distal end of the outer sheath in the delivery orientation, and the distal portion of the inner shaft is disposed outside of the outer sheath and the distal tip is distally spaced away from the distal end of the outer sheath in the deployed orientation, and wherein the outer sheath and the pusher shaft are configured to simultaneously move in opposing axial directions between the delivery orientation and the deployed orientation via actuation of the actuator to compensate for the foreshortening of the self-expanding prosthesis during deployment.

13. The system of claim 12, wherein the self-expanding prosthesis is a heart valve prosthesis.

14. The system of claim 12, wherein the self-expanding prosthesis is configured to foreshorten a first distance during deployment thereof and the pusher shaft is configured to distally advance the self-expanding prosthesis the first distance during deployment.

15. The system of claim 12, wherein the outer sheath and the pusher shaft are configured to simultaneously move in opposing axial directions at different rates, the pusher shaft being configured to move at a lower rate than the outer sheath.

16. The system of claim 12, wherein the pusher shaft is configured to advance at a rate profile that corresponds with a rate of foreshortening of the self-expanding prosthesis.

17. The system of claim 12, wherein actuation of the actuator in a first direction results in the outer sheath being proximally retracted and the pusher shaft being distally advanced and actuation of the actuator in a second direction results in the outer sheath being distally advanced and the pusher shaft being proximally retracted.

18. The system of claim 12, wherein the actuator is a rotatable housing of the handle.

19. The system of claim 12, wherein the distal portion of the inner shaft is disposed within the outer sheath and the distal tip engages and is distal to the distal end of the outer sheath in the delivery orientation, and the distal portion of the inner shaft is disposed outside of the outer sheath and the distal tip is distally spaced away from the distal end of the outer sheath in the deployed orientation.

* * * * *